United States Patent
Ou

(10) Patent No.: US 6,554,843 B1
(45) Date of Patent: Apr. 29, 2003

(54) CATARACT INSTRUMENT

(75) Inventor: Shu-Fong Ou, Taipei (TW)

(73) Assignee: Universal Optical Co., Ltd., Taipei (TW)

( * ) Notice: Subject to any disclaimer, the term of this patent is extended or adjusted under 35 U.S.C. 154(b) by 0 days.

(21) Appl. No.: 09/977,471

(22) Filed: Oct. 15, 2001

(51) Int. Cl.[7] .............................. A61B 17/24; A61F 9/00
(52) U.S. Cl. .................................. 606/113; 606/107
(58) Field of Search .......................... 606/106, 107, 606/108, 110, 113

(56) References Cited

U.S. PATENT DOCUMENTS

| | | | | |
|---|---|---|---|---|
| 614,854 A | * | 11/1898 | Kratzmueller et al. | 606/108 |
| 4,726,367 A | * | 2/1988 | Shoemaker | 606/107 |
| 5,066,297 A | * | 11/1991 | Cumming | 606/107 |
| 5,098,439 A | * | 3/1992 | Hill et al. | 606/107 |
| 5,171,314 A | * | 12/1992 | Dulebohn | 606/113 |
| 5,219,350 A | * | 6/1993 | Emerson et al. | 606/107 |
| 5,741,270 A | * | 4/1998 | Hansen et al. | 606/108 |
| 5,902,314 A | * | 5/1999 | Koch | 606/160 |
| 6,156,042 A | * | 12/2000 | Aramant | 606/107 |
| 6,245,078 B1 | * | 6/2001 | Ouchi | 606/113 |

* cited by examiner

Primary Examiner—Pedro Philogene
Assistant Examiner—David A Bonderer
(74) Attorney, Agent, or Firm—Thorp Reed & Armstrong LLP

(57) ABSTRACT

A cataract instrument has a tubular body. The tubular body has an aperture defined at a tapering front end thereof and an end cover provided at a rear and thereof. A shaft is received in the tubular body and has a loop formed at a front end of the shaft. Two flexible leaves are oppositely mounted on the tubular body and operatively mounted on the shaft. A resilient member is mounted between a rear end of the shaft and the end cover. When the flexible leaves are pressed, the shaft is moved forward and the loop is extended out from the aperture to attach with a cataract opaque tissue in a patient's eye. Then, the flexible leaves are released, the shaft is pulled backward by the resilient member and the loop is retracted in the tubular body to remove the cataract opaque tissue.

5 Claims, 2 Drawing Sheets

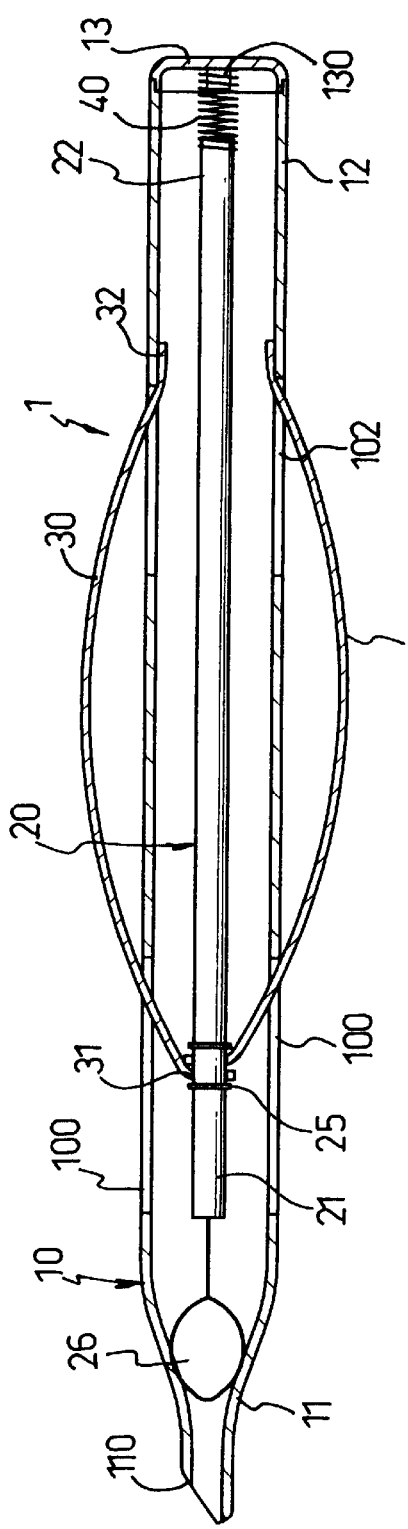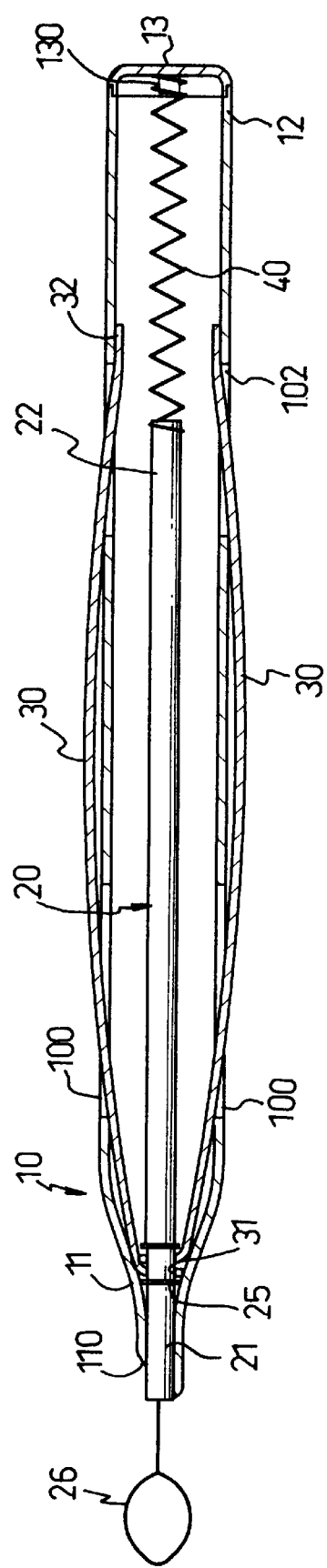

CATARACT INSTRUMENT

BACKGROUND OF THE INVENTION

1. Field of the Invention

The present is related to a medical instrument, and more particularly to an instrument for removing a cataract in an eye.

2. Description of Related Art

Cataracts are opaque tissue which has grown in a lens of an eye causing a loss of sight. In an operation for recovering a cataract patient's sight, a doctor removes the opaque tissue by a bistoury and plants an artificial lens in the patient's eye. However, healthy tissue around the diseased tissue often is removed by the bistoury because the lens has a round profile. Furthermore, it is also not easy to completely remove the irregularly-shaped diseased tissue using the conventional bistoury.

Therefore, the invention provides a cataract instrument to mitigate and/or obviate the aforementioned problems.

SUMMARY OF THE INVENTION

The main objective of the invention is to provide a cataract instrument with which a doctor can effectively remove opaque tissue in a patient's eye.

Other objects, advantages and novel features of the invention will become more apparent from the following detailed description when taken in conjunction with the accompanying drawings.

BRIEF DESCRIPTION OF THE DRAWINGS

FIG. 2 is a cross sectional view of the cataract instrument in FIG. 1, and in a retracted mode; and FIG. 3 is a cross sectional view showing that the cataract instrument is in an extended mode.

DETAILED DESCRIPTION OF THE PREFERRED EMBODIMENT

Figure 1:
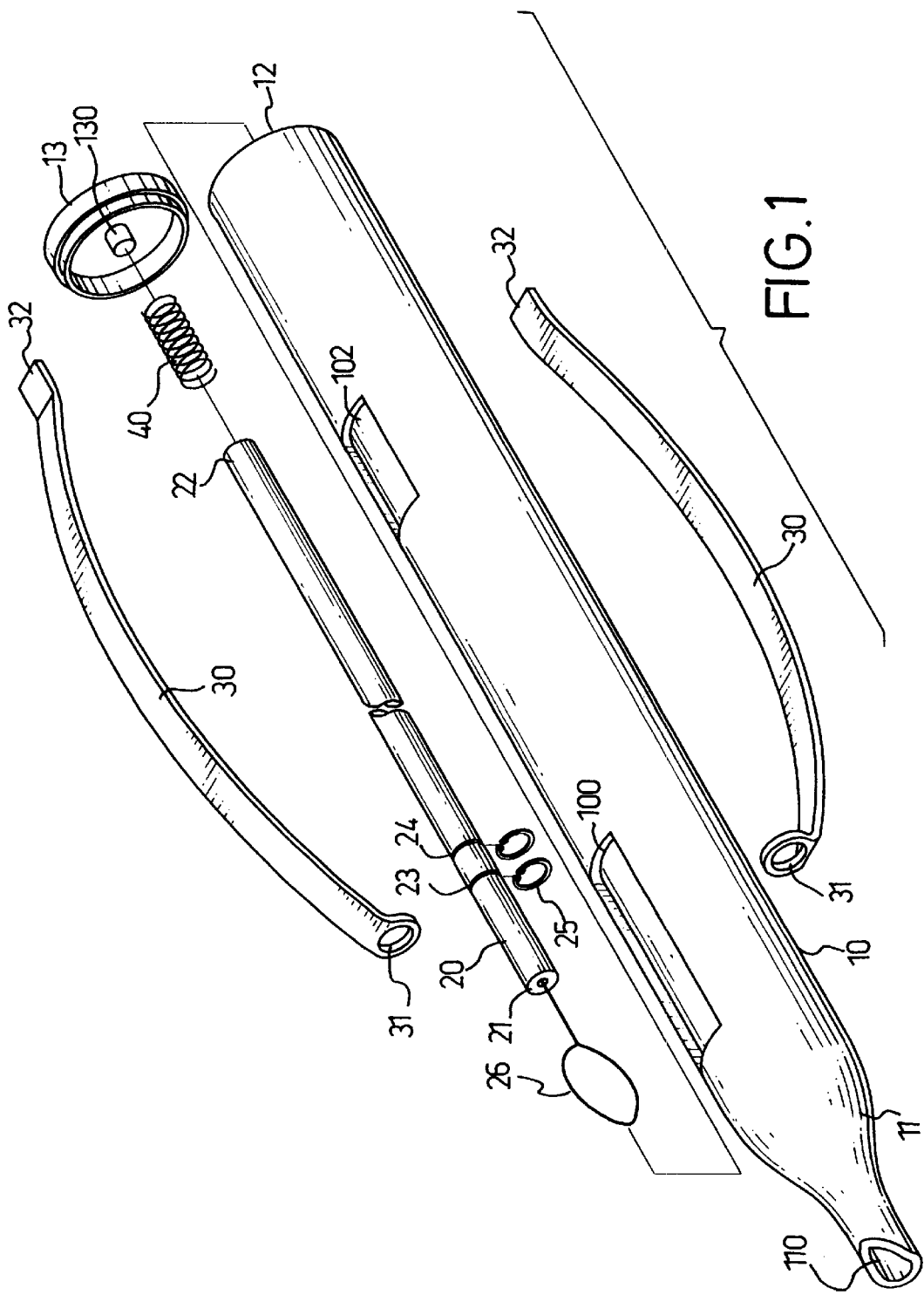
FIG. 1 is an exploded perspective view of a cataract instrument in accordance with the invention.

Referring to FIGS. 1 and 2, a cataract instrument (1) in accordance with the invention is composed of a tubular body (10), a shaft (20), two flexible leaves (30) and a resilient member (40).

The tubular body (10) has a tapering front end (11) and an aperture (110) is defined through the front end (11). An end cover (13) is provided at a rear end (12) of the tubular body (10). A pole (130) is formed at the center of the end cover (13) for fastening the resilient member (40). Two pairs of openings (100, 102) are oppositely defined through an outer periphery of the tubular body (10).

The shaft (20) is received in the tubular body (10) and has two ring recesses (23, 24) defined in an outer periphery thereof and near a front end (21) thereof. Two collars (25) are respectively secured in the ring recesses (23, 24). A loop (26) made of elastic metal such as a stainless alloy steel is provided on the front end (21) and received in the tubular body (10).

Each flexible leaf (30) has a ring (31) formed at a front end thereof and a flat portion (32) formed at a rear end thereof. The front ends of the flexible leaves (30) are respectively inserted into the front openings (100) and the rings (31) are fastened between the collars (25). The flat portions (32) of the flexible leaves (30) are respectively inserted into the rear openings (102) and abut an inner wall of the tubular body (10).

The resilient member (40) is secured between a rear end (22) of the shaft (20) and the pole (130) of the end cover (30). The resilient member (40) is also made of a stainless alloy steel.

Referring to FIG. 3, when the flexible leaves (30) are pressed to move the shaft (20) forward, the loop (26) is deformed and extends out the tubular body (10) through the aperture (26). The resilient member (40) is stretched according to the moving of the shaft (20). Because the loop (26) is made of the elastic metal, the loop (26) will return to the original shape after extending out the tubular body (10).

When the flexible leaves (30) are released, under the force of the resilient member (40), the shaft (20) is moved backward and the loop (26) is retracted in the tubular body (10).

In operation, the flexible leaves (30) are pressed and the loop (26) is extended out from the tubular body (10) to grip an opaque tissue that needs to be removed from a patient's eye. Afterward, the flexible leaves (30) are released to retract the loop (26) in tile tubular body (10), and the opaque tissue attached is removed.

It is to be understood, however, that even though numerous characteristics and advantages of the present invention have been set forth in the foregoing description, together with details of the structure and function of the invention, tile disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A cataract instrument (1) comprising:

a tubular body (10) having a tapering front end (11), a rear end (12), an aperture (110) defined at the tapering front end (11), an end cover (13) mounted on the rear end (12), and two pairs of openings (100, 102) oppositely defined through an outer periphery of the tubular body (10);

a shaft (20) received in the tubular body (10), the shaft (20) having a front end (21), a rear end (22), two ring recesses (23, 24) defined in an outer periphery of the shaft (20) and near the front end (21), two collars (25) respectively secured in the ring recesses (23, 24), and a loop (26) formed at the front end (21);

two flexible leaves (30) oppositely mounted on the tubular body (10), each flexible leaf (30) having a front end inserted into the respective front opening (100), a rear end inserted into the respective rear opening (102), a ring (31) formed at the front end and secured between the collars (25), and a flat portion (32) abutting an inner wall of the tubular body (10); and a resilient member (40) mounted between the end cover (13) and the rear end (22), whereby, when the flexible leaves (30) are pressed towards the tubular body, the shaft (20) is moved forward and the loop (26) is extended out from the aperture (110) to grip an opaque tissue in a patient's eye, and then the flexible leaves (30) are released, the shaft (20) is pulled backward by the resilient member (40) and the loop (26) is retracted in the tubular body (10) to remove the opaque tissue.

2. The cataract instrument as claimed in claim 1, wherein the end cover (13) further has a pole (130) formed at the center thereof and the resilient member (40) is secured on the pole (130).

3. The cataract instrument as claimed in claim 1, wherein the loop (26) is made of a stainless alloy metal.

4. The cataract instrument as claimed in claim 1, wherein the resilient member (40) is a spring.

5. The cataract instrument as claimed in claim 4, wherein the spring is made of a stainless alloy metal.

\* \* \* \* \*